(12) United States Patent
Bruchman et al.

(10) Patent No.: US 9,144,492 B2
(45) Date of Patent: Sep. 29, 2015

(54) TRUNCATED LEAFLET FOR PROSTHETIC HEART VALVES, PREFORMED VALVE

(71) Applicant: W. L. Gore & Associates, Inc., Newark, DE (US)

(72) Inventors: William C. Bruchman, Camp Verde, AZ (US); Cody L. Hartman, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 41 days.

(21) Appl. No.: 13/843,196

(22) Filed: Mar. 15, 2013

(65) Prior Publication Data

US 2014/0172080 A1 Jun. 19, 2014

Related U.S. Application Data

(60) Provisional application No. 61/739,721, filed on Dec. 19, 2012.

(51) Int. Cl.
*A61F 2/24* (2006.01)

(52) U.S. Cl.
CPC ............. *A61F 2/2412* (2013.01); *A61F 2/2415* (2013.01); *A61F 2230/0023* (2013.01); *A61F 2230/0026* (2013.01)

(58) Field of Classification Search
USPC .................................. 623/2.34, 2.37, 2.3, 2.1
See application file for complete search history.

(56) References Cited

U.S. PATENT DOCUMENTS

| | | | |
|---|---|---|---|
| 4,265,694 A | 5/1981 | Boretos et al. | |
| 5,628,791 A | 5/1997 | Bokros et al. | |
| 6,174,331 B1 | 1/2001 | Moe et al. | |
| 6,283,994 B1 | 9/2001 | Moe et al. | |
| 6,283,995 B1 | 9/2001 | Moe et al. | |
| 6,328,763 B1 | 12/2001 | Love et al. | |
| 6,454,798 B1 | 9/2002 | Moe | |
| 6,482,228 B1 | 11/2002 | Norred | |
| 6,562,069 B2 | 5/2003 | Cai et al. | |
| 6,613,086 B1 | 9/2003 | Moe et al. | |
| 6,666,885 B2 | 12/2003 | Moe | |
| 6,916,338 B2 | 7/2005 | Speziali | |

(Continued)

FOREIGN PATENT DOCUMENTS

| | | |
|---|---|---|
| FR | 2 591 100 | 6/1987 |
| WO | 00/62716 | 10/2000 |

(Continued)

OTHER PUBLICATIONS

International Search Report for PCT/US2013/076688 mailed Feb. 27, 2014, corresponding to U.S. Appl. No. 14/133,563, 5 pages.

(Continued)

*Primary Examiner* — Thomas J Sweet
*Assistant Examiner* — Wade P Schutte
(74) *Attorney, Agent, or Firm* — Paul J. Fordenbacher, Esq.

(57) ABSTRACT

Described embodiments are directed toward prosthetic valves having leaflets of a particular shape that improves bending character without requiring a long length valve. In accordance with an embodiment, a prosthetic valve comprises a leaflet frame, a plurality of leaflets that are coupled to the leaflet frame, where each leaflet has a free edge and a base. The base of each leaflet is truncated in which the leaflet in cross section shows a line in an alpha plane onto the leaflet frame.

21 Claims, 9 Drawing Sheets

(56) References Cited

U.S. PATENT DOCUMENTS

| | | |
|---|---|---|
| 7,381,218 B2 | 6/2008 | Schreck |
| 7,462,675 B2 * | 12/2008 | Chang et al. .................. 526/247 |
| 7,510,575 B2 | 3/2009 | Spenser et al. |
| 7,780,725 B2 | 8/2010 | Haug et al. |
| 7,967,853 B2 | 6/2011 | Eidenschink et al. |
| 7,993,394 B2 | 8/2011 | Hariton et al. |
| 8,728,154 B2 * | 5/2014 | Alkhatib ..................... 623/2.17 |
| 8,961,599 B2 | 2/2015 | Bruchman et al. |
| 2002/0082687 A1 | 6/2002 | Moe |
| 2004/0024448 A1 | 2/2004 | Chang et al. |
| 2006/0290027 A1 | 12/2006 | O'Connor et al. |
| 2007/0010876 A1 | 1/2007 | Salahieh et al. |
| 2007/0207186 A1 | 9/2007 | Scanlon et al. |
| 2008/0133004 A1 | 6/2008 | White |
| 2008/0220041 A1 | 9/2008 | Brito et al. |
| 2010/0036021 A1 | 2/2010 | Lee et al. |
| 2010/0082094 A1 | 4/2010 | Quadri et al. |
| 2010/0191320 A1 | 7/2010 | Straubinger et al. |
| 2010/0217382 A1 | 8/2010 | Chau et al. |
| 2010/0262231 A1 | 10/2010 | Tuval et al. |
| 2011/0208283 A1 | 8/2011 | Rust |
| 2011/0218619 A1 | 9/2011 | Benichou et al. |
| 2011/0251678 A1 | 10/2011 | Eidenschink et al. |
| 2012/0101571 A1 | 4/2012 | Thambar et al. |
| 2012/0130471 A1 | 5/2012 | Shoemaker et al. |
| 2012/0323315 A1 | 12/2012 | Bruchman et al. |
| 2014/0180400 A1 | 6/2014 | Bruchman et al. |
| 2014/0236289 A1 | 8/2014 | Alkhatib |

FOREIGN PATENT DOCUMENTS

| | | |
|---|---|---|
| WO | 2008/097592 | 8/2008 |
| WO | 2012/082952 | 6/2012 |
| WO | 2012/110767 | 8/2012 |
| WO | 2012/167131 | 12/2012 |
| WO | 2014/018432 | 1/2014 |

OTHER PUBLICATIONS

International Search Report for PCT/US2013/074962 mailed Feb. 27, 2014, corresponding to U.S. Appl. No. 13/833,650, 4 pages.

International Search Report for PCT/US2013/068390 mailed Apr. 29, 2014, corresponding to U.S. Appl. No. 13/835,988, 7 pages.

International Search Report for PCT/US2013/076504 mailed Feb. 27, 2014, corresponding to U.S. Appl. No. 14/133,491, 7 pages.

International Search Report for PCT/US2013/071632 mailed Mar. 18, 2014, corresponding to U.S. Appl. No. 13/841,334, 6 pages.

International Search Report for PCT/US2013/075274 mailed Feb. 27, 2014, corresponding to U.S. Appl. No. 13/843,196, 5 pages.

International Search Report for PCT/US2013/075380 mailed , corresponding to U.S. Appl. No. 13/869,524, 5 pages.

International Search Report for PCT/US2013/068780 mailed Feb. 27, 2014, corresponding to U.S. Appl. No. 13/869,878, 4 pages.

International Search Report for PCT/US2013/075380 mailed Mar. 3, 2014, corresponding to U.S. Appl. No. 13/869,524, 5 pages. (previously submitted on Aug. 7, 2014).

International Search Report for PCT/US2013/076504 mailed Apr. 28, 2014, corresponding to U.S. Appl. No. 14/133,491, 7 pages. (previously submitted on Aug. 7, 2014).

International Search Report for PCT/US2013/071632 mailed Apr. 28, 2014, corresponding to U.S. Appl. No. 13/841,334, 6 pages. (previously submitted on Aug. 7, 2014).

International Search Report for PCT/US2013/075380 mailed Mar. 6, 2014, corresponding to U.S. Appl. No. 13/869,524, 5 pages. (previously submitted on Aug. 7, 2014).

Clough, Norman E. introducing a New Family of GORE™ ePTFE Fibers (2007).

* cited by examiner

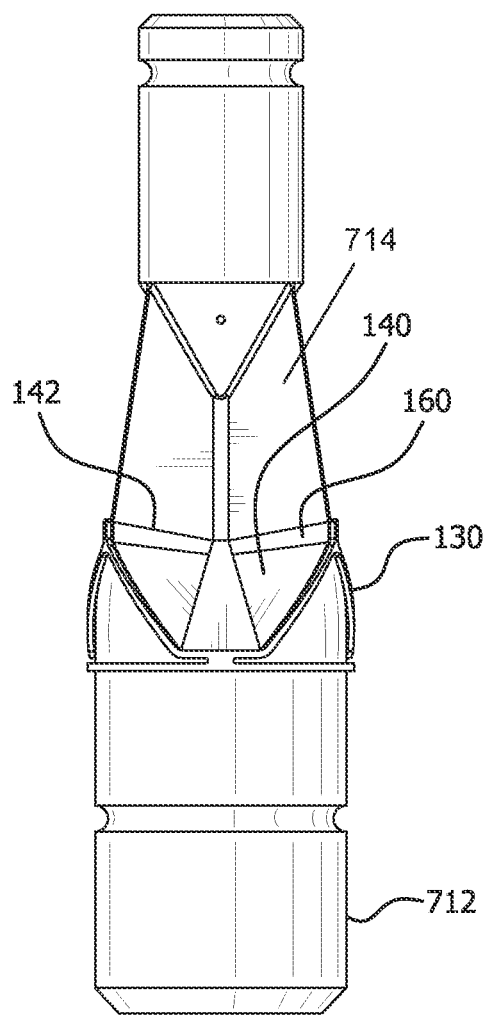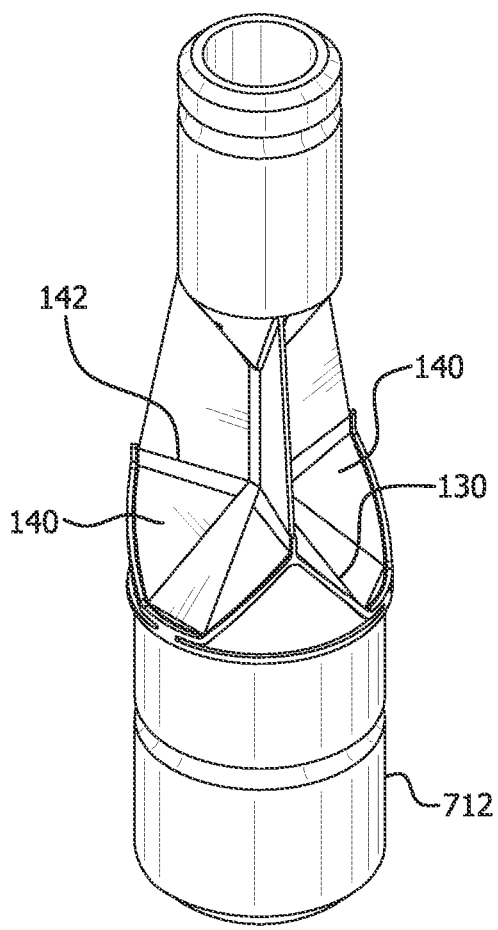
FIG. 6A
FIG. 6B

TRUNCATED LEAFLET FOR PROSTHETIC HEART VALVES, PREFORMED VALVE

CROSS-REFERENCE TO RELATED APPLICATIONS

This application claims priority to U.S. provisional patent application Ser. No. 61/739,721 filed Dec. 19, 2012, which is herein incorporated by reference in its entirety.

FIELD

The present disclosure relates generally to prosthetic valves and more specifically synthetic flexible leaflet-type prosthetic valve devices, systems, and methods.

BACKGROUND

Bioprosthetic valves have been developed that attempt to mimic the function and performance of a native valve. Flexible leaflets are fabricated from biological tissue such as bovine pericardium. In some valve designs the biological tissue is sewn onto a relatively rigid frame that supports the leaflets and provides dimensional stability when implanted. Although bioprosthetic valves can provide excellent hemodynamic and biomechanical performance in the short term, they are prone to calcification and cusp tears, among other failure modes, requiring reoperation and replacement.

Attempts have been made to use synthetic materials, such as polyurethane, among others, as a substitute for the biological tissue, to provide a more durable flexible leaflet prosthetic valve, herein referred to as a synthetic leaflet valve (SLV). However, synthetic leaflet valves have not become a valid valve replacement option since they suffer premature failure, due to, among other things, suboptimal design and lack of a durable synthetic material.

The leaflet moves under the influence of fluid pressure. In operation, the leaflets open when the upstream fluid pressure exceeds the downstream fluid pressure and close when the downstream fluid pressure exceeds the upstream fluid pressure. The free edges of the leaflets coapt under the influence of downstream fluid pressure closing the valve to prevent downstream blood from flowing retrograde through the valve.

A preferred shape of synthetic heart valve leaflets has been described many times, but each is different from the others. The various three-dimensional shapes range from spherical or cylindrical to truncated conical intersections with spheres and an "alpharabola".

SUMMARY

Described embodiments are directed to an apparatus, system, and methods for valve replacement, such as cardiac valve replacement. More specifically, described embodiments are directed toward flexible leaflet valve devices in which a truncated segment at the base of the leaflet is present at or adjacent to the intersection with the frame.

In accordance with an embodiment, a prosthetic valve comprises a leaflet frame, a plurality of leaflets that are coupled to the leaflet frame, where each leaflet has a free edge and a base. The base of each leaflet is truncated in which the leaflet in cross section shows a line in an alpha plane onto the leaflet frame.

In accordance with an embodiment, a prosthetic valve comprises a frame having a generally tubular shape with attached film. The frame defines a plurality of leaflet windows. The film defines at least one leaflet extending from each of the leaflet windows. Each leaflet two leaflet sides, a planar central zone, a leaflet base and a free edge opposite the leaflet base. The two leaflet sides diverge from the leaflet base.

BRIEF DESCRIPTION OF THE DRAWINGS

The accompanying drawings are included to provide a further understanding of the present disclosure and are incorporated in and constitute a part of this specification, illustrate embodiments described herein, and together with the description serve to explain the principles discussed in this disclosure.

FIG. 6A is a side view of the leaflet frame on a cutting mandrel, in accordance with an embodiment;
and
FIG. 6B is a perspective view of the leaflet frame on the assembly mandrel of FIG. 6A.

DETAILED DESCRIPTION

Figure 1A:
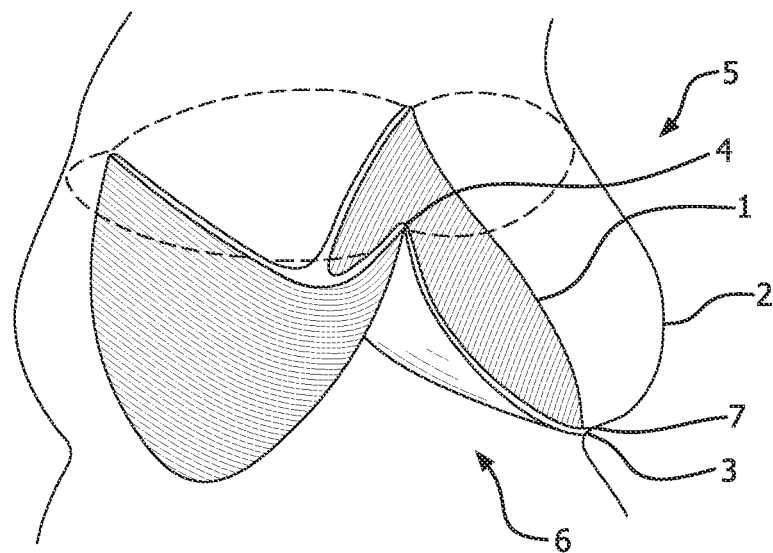
FIG. 1A is a sketch of an aortic valve.

Persons skilled in the art will readily appreciate that various aspects of the present disclosure can be realized by any number of methods and apparatus configured to perform the intended functions. Stated differently, other methods and apparatuses can be incorporated herein to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

Although the embodiments herein may be described in connection with various principles and beliefs, the described embodiments should not be bound by theory. For example, embodiments are described herein in connection with prosthetic valves, more specifically cardiac prosthetic valves. However, embodiments within the scope of this disclosure can be applied toward any valve or mechanism of similar structure and/or function. Furthermore, embodiments within the scope of this disclosure can be applied in non-cardiac applications.

The term leaflet as used herein in the context of prosthetic valves is a component of a one-way valve wherein the leaflet is operable to move between an open and closed position under the influence of a pressure differential. In an open position, the leaflet allows blood to flow through the valve. In a closed position, the leaflet substantially blocks retrograde flow through the valve. In embodiments comprising multiple leaflets, each leaflet cooperates with at least one neighboring leaflet to block the retrograde flow of blood. The pressure differential in the blood is caused, for example, by the contraction of a ventricle or atrium of the heart, such pressure differential typically resulting from a fluid pressure building up on one side of the leaflets when closed. As the pressure on an inflow side of the valve rises above the pressure on the outflow side of the valve, the leaflets opens and blood flows therethrough. As blood flows through the valve into a neighboring chamber or blood vessel, the pressure on the inflow side equalizes with the pressure on the outflow side. As the pressure on the outflow side of the valve raises above the blood pressure on the inflow side of the valve, the leaflet returns to the closed position generally preventing retrograde flow of blood through the valve.

The term membrane as used herein refers to a sheet of material comprising a single composition, such as, but not limited to, expanded fluoropolymer.

The term composite material as used herein refers to a combination of a membrane, such as, but not limited to, expanded fluoropolymer, and an elastomer, such as, but not limited to, a fluoroelastomer. The elastomer may be imbibed within a porous structure of the membrane, coated on one or both sides of the membrane, or a combination of coated on and imbibed within the membrane.

The term laminate as used herein refers to multiple layers of membrane, composite material, or other materials, such as elastomer, and combinations thereof.

The term film as used herein generically refers to one or more of the membrane, composite material, or laminate.

The term biocompatible material as used herein generically refers to a film or a biological material, such as, but not limited to, bovine pericardium.

The term leaflet window is defined as that space that a frame defines from which a leaflet extends. The leaflet may extend from frame elements or adjacent to frame elements and spaced apart therefrom.

The terms native valve orifice and tissue orifice refer to an anatomical structure into which a prosthetic valve may be placed. Such anatomical structure includes, but is not limited to, a location wherein a cardiac valve may or may not have been surgically removed. It is understood that other anatomical structures that may receive a prosthetic valve include, but are not limited to, veins, arteries, ducts and shunts. Although reference is made herein to replacing a native valve with a prosthetic valve, it is understood and appreciated that a valve orifice or implant site may also refer to a location in a synthetic or biological conduit that may receive a valve for a particular purpose, and therefore the scope of the embodiments provided herein is not limited to valve replacement.

As used herein, "couple" means to join, connect, attach, adhere, affix, or bond, whether directly or indirectly, and whether permanently or temporarily.

As used herein, truncated or truncation refers to the sectioning of a three-dimensional body with a plane reducing the size of the body. Referring to FIG. 2D, a truncation zone is that area that may be truncated by the alpha plane so as to define an attachment line 145, i.e., a line of attachment, of the leaflet base 143.

Embodiments herein include various apparatus, systems, and methods for a prosthetic valve suitable for surgical and transcatheter placement, such as, but not limited to, cardiac valve replacement. The valve is operable as a one-way valve wherein the valve defines a valve orifice into which leaflets open to permit flow and close so as to occlude the valve orifice and prevent flow in response to differential fluid pressure.

The length of a leaflet heart valve is dictated by the angle the leaflet makes with respect to the enclosing frame. A longer leaflet has a shallower angle with respect to the frame. A shorter leaflet has a steeper angle with respect to the frame. A longer leaflet leads to better performance than a shorter leaflet. For most applications however, only a short valve can fit into the recipient location. Thus the valve designer is presented with a dilemma. In the instant embodiments, leaflet designs are provided that provide for good performance with a short leaflet, thus allowing short heart valves.

Valve

Figure 1B:
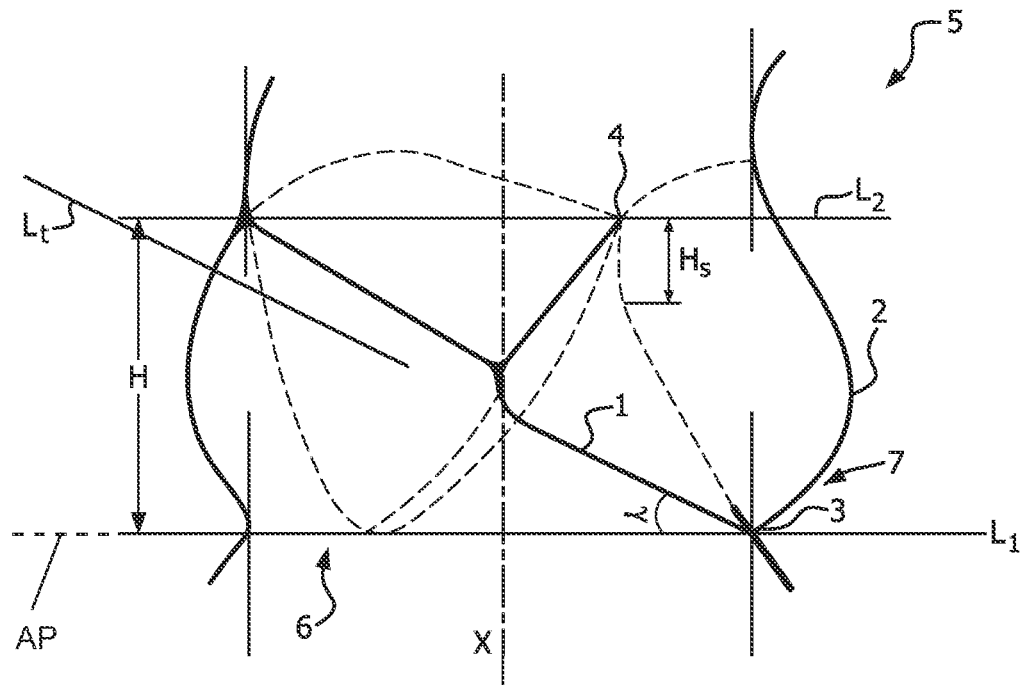
FIG. 1B is a cross-section of the aortic valve of FIG. 1A showing the angles associated with a leaflet heart valve.

FIG. 1A. is a sketch of an aortic valve 5. The leaflets 1 are coupled to the aortic root 2 at the leaflet base 3. FIG. 1B is a cross-section of the aortic valve 5 of FIG. 1A showing the angles associated with a leaflet 1 of the aortic valve 5. FIG. 1B illustrates the relationship between the leaflets 1 and a first horizontal line L1 extending through the leaflet base 3 at an attachment point 7, and a second horizontal line L2 extending through the tops 4 of the commissure. In FIG. 1B, the aortic valve 5 is oriented in a position with a valve axis X being vertical, the inflow edge 6 is pointed downward, with the leaflets 1 in the closed position. The attachment angle alpha (a) is defined as the angle between the tangent line Lt extending from the center of the leaflet base 3 of the leaflet 1 at the attachment point 7 and the first horizontal line L1 extending through the leaflet base 3 at the attachment point 7, as shown in FIG. 1.

It is understood that leaflets 1 may exhibit a concave, straight, or convex shape in an axial cross-section through the center of the leaflet base 3 of the leaflet 1 at the attachment point 7. For the sake of clarity and simplification of description of the embodiments presented herein and not limited thereto, the geometry of a leaflet 1 is described as having, in an axial cross-section through the center of the leaflet base 3 of the leaflet 1 at the attachment point 7, the tangent line Lt that defines a as a straight line.

Figure 2A:
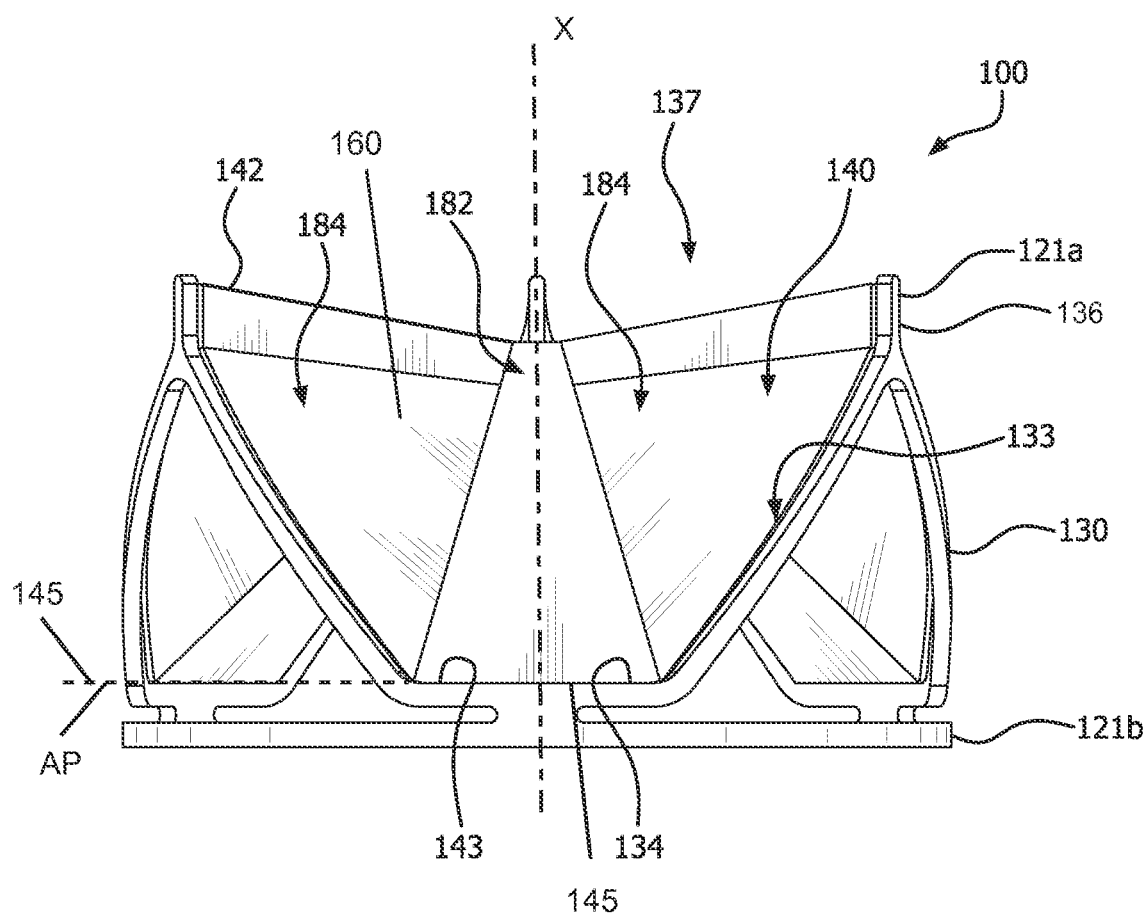
FIG. 2A is a side view of a prosthetic valve in accordance with an embodiment.
Figure 2B:
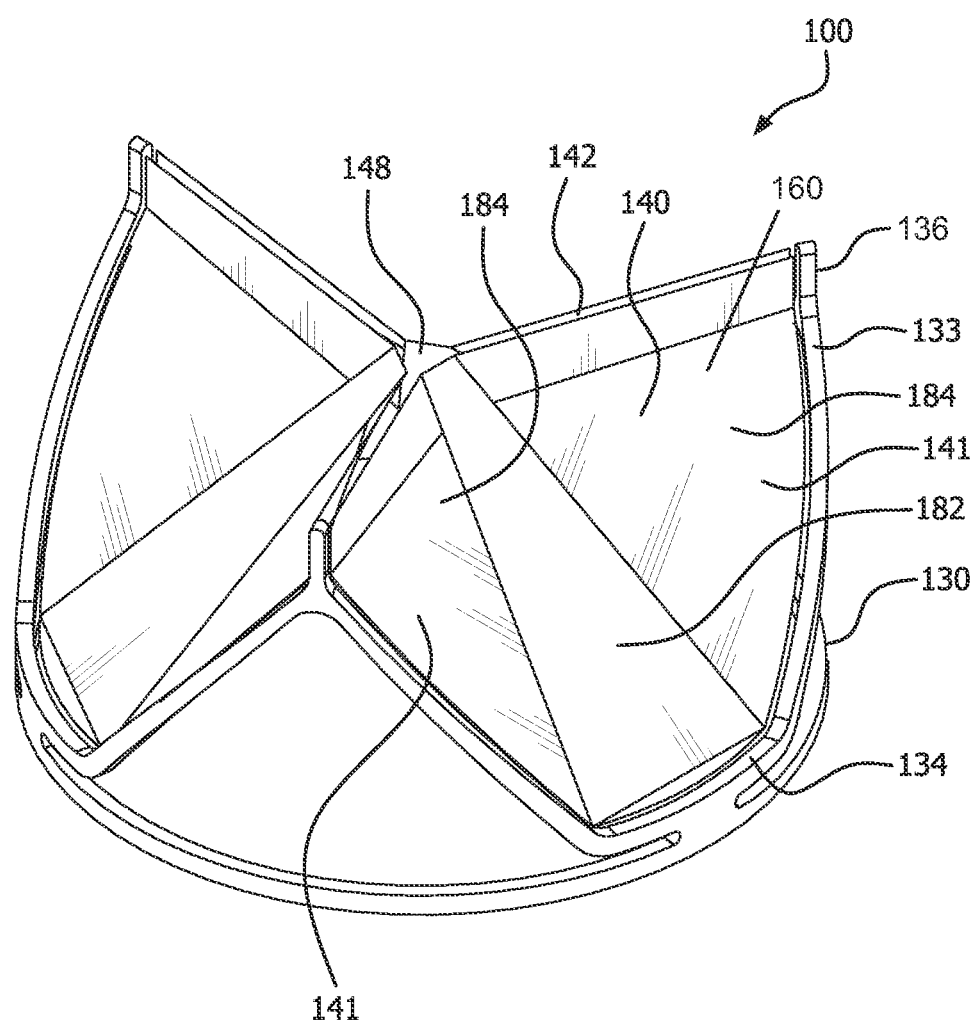
FIG. 2B is a perspective view of the embodiment of the valve of FIG. 2A.
Figure 2C:
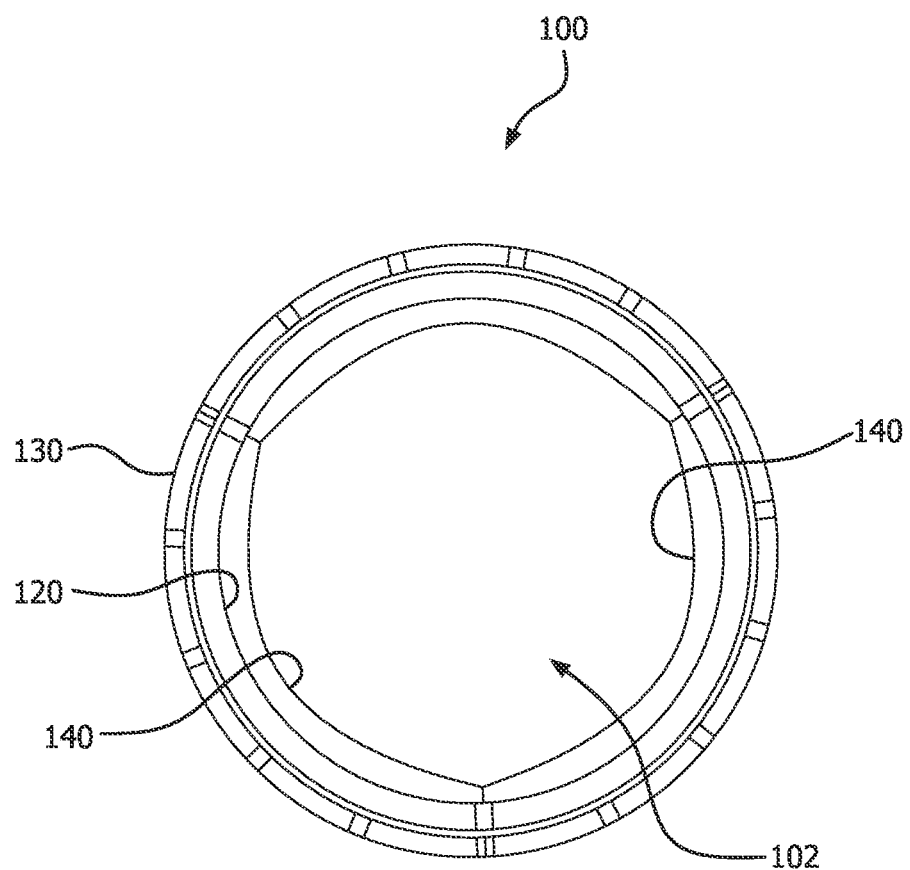
FIG. 2C is an axial view of an embodiment of a prosthetic valve in an open configuration.
Figure 2D:
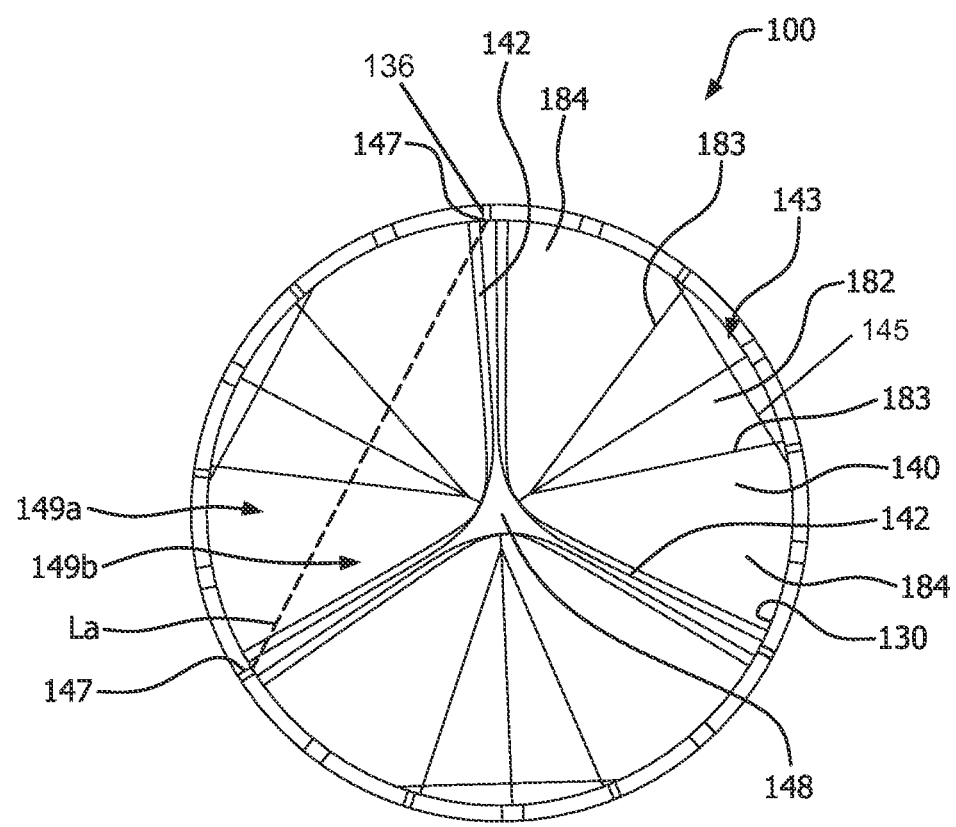
FIG. 2D is an axial view of the embodiment of the prosthetic valve of FIG. 2A in a closed configuration.
Figure 3:
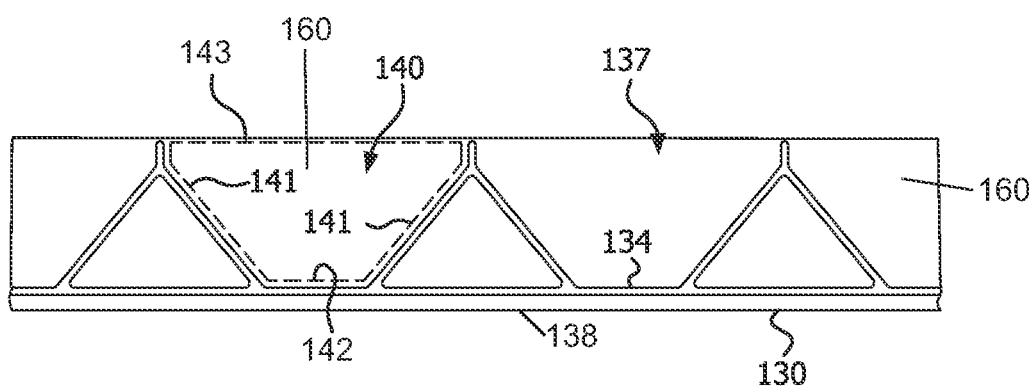
FIG. 3 is a representation of an embodiment of a leaflet frame unrolled to a flat orientation.

FIG. 2A is a side view of a prosthetic valve 100, in accordance with an embodiment. FIG. 2B is a perspective view of the prosthetic valve 100 of FIG. 2A. FIGS. 2C and 2D are axial views of the prosthetic valve 100 of FIG. 2A in an open and closed configuration, respectively. FIG. 3 is a side view of a leaflet frame 130 of the prosthetic valve 100 of FIG. 2A wherein the leaflet frame 130 has been longitudinally cut and laid open to better illustrate the elements of the generally tubular-shaped prosthetic valve 100. In FIGS. 2A and 2B, the leaflets 140 are shown slightly open as they are when held by the cutting mandrel 712. It is understood that a fully closed prosthetic valve 100 will have the leaflet free edges 142 of the leaflets 140, including the triple point 148, coming together to coapt under the influence of downstream fluid pressure which results in closing the valve to prevent downstream blood from flowing retrograde through the valve.

Embodiments provided herein provide a solution to the tension between desiring a small alpha angle to have a short valve and a larger alpha angle resulting in longer leaflets for better leaflet bending behavior. Embodiments provided herein provide a larger alpha angle while reducing valve length, by providing a leaflet that wherein the leaflet base 3 is truncated, providing a relatively flat leaflet base 143.

In accordance with embodiments herein, the attachment angle alpha (a) of a given valve configuration is preserved as the leaflet height is reduced. This is accomplished by redefining the base of the leaflet not as an attachment point 7 as for the generally parabolic leaflet shape as shown in FIG. 1A, but as an attachment line 145 as shown in FIGS. 2A and 2D, that is parallel to the horizontal line in the valve cross sectional plane perpendicular to the valve axis X at the leaflet base 143 of the leaflet 140.

As a way to visualize embodiments provided herein, referring to FIG. 1B, the first horizontal line L1 extends through the leaflet base 3 as it moves perpendicular along the valve axis X towards the commissure tops 4. A plane containing the first horizontal line L1 and perpendicular to the valve axis X, referred to as the alpha plane AP, intersects the leaflet 140 of FIG. 2A along a line of attachment 145. The leaflet base 3 truncated by the alpha plane AP, where the attachment point 7 of the leaflet base 3 becomes an attachment line 145, that is, a line of attachment rather than a point, of the leaflet base 143 as shown in FIGS. 2A, 2B and 2D, as compared with leaflet base 3 of the leaflet 1 at the attachment point 7 shown in FIG. 1A.

Referring to FIG. 2D, an apex line La is indicated connecting the apices 147 of the leaflets 140. The apex line La divides the leaflet 140 into a first region 149a adjacent the leaflet frame 130, and a second region 149b adjacent the leaflet free edge 142. The first region 149a defines a truncated zone. The truncated zone is located on the lower section of the leaflet 140 adjacent the leaflet base 143. The truncation zone is that area that may be truncated by the alpha plane AP so as to define an attachment line 145, that is, a line of attachment, of the leaflet base 143.

Frame

Referring to FIGS. 2A-2D, the leaflet frame 130 is a generally tubular member defining a generally open pattern of apertures 122, in accordance with an embodiment. In accordance with transcatheter embodiments, the leaflet frame 130 is operable to allow it 120 to be compressed and expanded between different diameters. The leaflet frame 130 comprises a frame first end 121a and a frame second end 121b opposite the frame first end 121a. The leaflet frame 130 comprises a leaflet frame outer surface 126a and a leaflet frame inner surface 126b opposite the leaflet frame outer surface 126a, as shown in FIG. 2A. The leaflet frame 130 defines commissure posts 136 that couple to the leaflet free edges 142.

The leaflet frame 130 may comprise a structure known in the art as a stent. A stent is a tubular member that may have a small diameter suitable for percutaneous transcatheter delivery into the anatomy, and may be expanded to a larger diameter when deployed into the anatomy. Stents having various designs and material properties are well known in the art.

The leaflet frame 130 can define any number of features, repeatable or otherwise, such as geometric shapes and/or linear or meandering series of sinusoids. Geometric shapes can comprise any shape that facilitates substantially uniform circumferential compression and expansion. The leaflet frame 130 may comprise a cut tube, or any other element suitable for the particular purpose. The leaflet frame 130 may be etched, cut, laser cut, or stamped into a tube or a sheet of material, with the sheet then formed into a substantially cylindrical structure. Alternatively, an elongated material, such as a wire, bendable strip, or a series thereof, can be bent or braided and formed into a substantially cylindrical structure wherein the walls of the cylinder comprise an open framework that is compressible to a smaller diameter in a generally uniform and circumferential manner and expandable to a larger diameter.

The leaflet frame 130 can comprise any metallic or polymeric biocompatible material. For example, the leaflet frame 130 can comprise a material, such as, but not limited to nitinol, cobalt-nickel alloy, stainless steel, or polypropylene, acetyl homopolymer, acetyl copolymer, ePTFE, other alloys or polymers, or any other biocompatible material having adequate physical and mechanical properties to function as described herein.

Figure 4A:
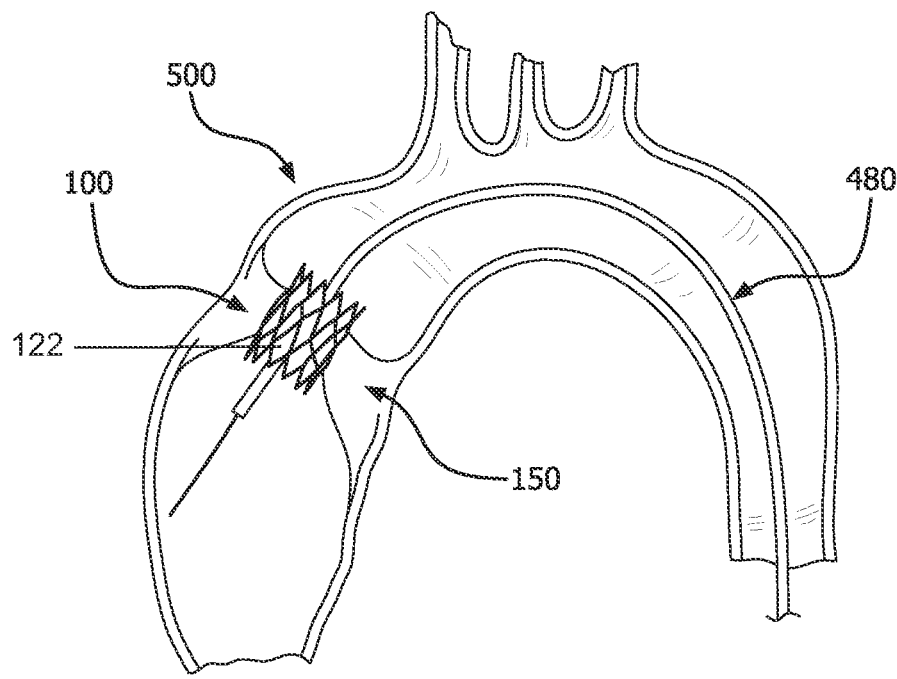
FIG. 4A is a side view of an embodiment of a transcatheter delivery system within anatomy.
Figure 4B:
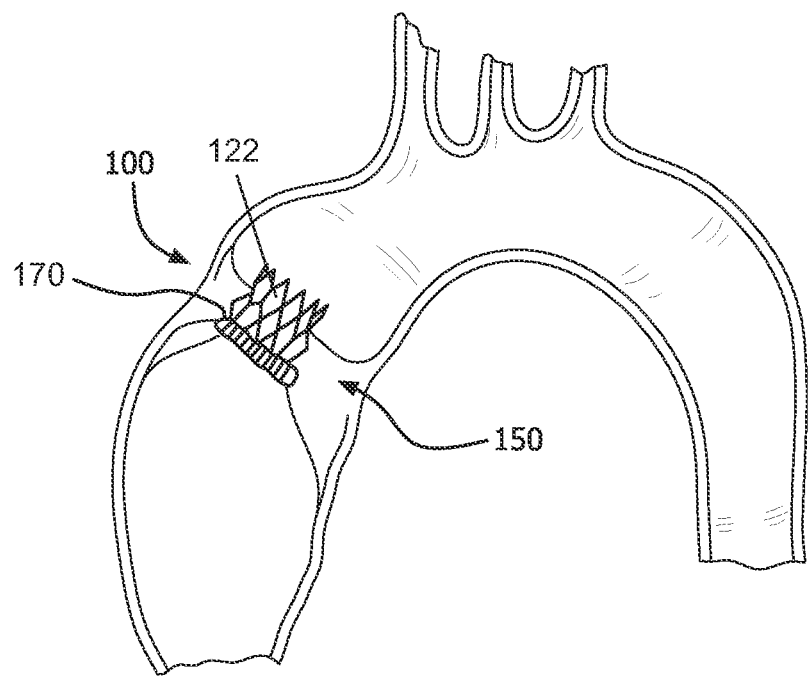
FIG. 4B is a side view of an embodiment of a surgical valve within anatomy.

In accordance with embodiments, the leaflet frame 130 can be configured to provide positive engagement with an implant site to firmly anchor the prosthetic valve 100 to the site, as shown in FIG. 4A representing a transcatheter deployment of the prosthetic valve 100. In accordance with an embodiment, the leaflet frame 130 can comprise a sufficiently rigid frame having small elastic recoil so as to maintain sufficient apposition against a tissue orifice 150 to maintain position. In accordance with another embodiment, the leaflet frame 130 can be configured to expand to a diameter that is larger than a tissue orifice 150 so that when prosthetic valve 100 expands into the tissue orifice 150, it can be firmly seated therein. In accordance with another embodiment, the leaflet frame 130 can comprise one or more anchors (not shown) configured to engage the implant site, such as a tissue orifice 150, to secure the prosthetic valve 100 to the implant site.

It is appreciated that other elements or means for coupling the prosthetic valve 100 to an implant site are anticipated. By way of example, but not limited thereto, other means, such as mechanical and adhesive means may be used to couple the prosthetic valve 100 to a synthetic or biological conduit.

As will be discussed later, the surgical prosthetic valve 100 embodiment may or may not have the zigzag configuration since the surgical prosthetic valve 100 may be of a fixed diameter and need not be operable to compress and re-expand.

FIG. 3 is a side view of the leaflet frame 130 wherein the leaflet frame 130 has been longitudinally cut and laid open to better illustrate the elements of the leaflet frame 130 of the prosthetic valve 100 of FIG. 2B. The leaflet frame 130 comprises a base element 138 and a plurality of spaced apart isosceles triangle elements 174 interconnected by the base element 138. Each leaflet window 137 is defined by a leaflet window 133 which is a side 175 of one triangle element 174 and another leaflet window side 133 which is a side 175 of an adjacent triangle element 174, and wherein each leaflet window base 134 is defined by the base element 138, wherein each leaflet window 137 defines an isosceles trapezoid. In accordance with an embodiment of the prosthetic valve 100, each leaflet 140 has substantially the shape of an isosceles trapezoid having two leaflet sides 141, a leaflet base 143 and a leaflet free edge 142 opposite the leaflet base 143, wherein the two leaflet sides 141 diverge from the leaflet base 143, wherein the leaflet base 143 is substantially flat, as shown in dashed lines in FIG. 3. The leaflet frame 130 further defines commissure posts 136 from which the leaflet free edge 142 extends.

In accordance with an embodiment, the leaflet frame 130 comprises a frame first end and a frame second end opposite the frame first end, the leaflet window having a shape determined, at least in part, by wrapping a two dimensional isosceles trapezoid onto the tubular shape of the frame, the isosceles trapezoid having a base and two sides that diverge from the base, and wherein a side from adjacent isosceles trapezoids meet at the frame second end.

In transcatheter prosthetic valve 100 embodiments, the leaflet frame 130 is elastically, plastically, or both, compressible to obtain a relatively small diameter to accommodate percutaneous transcatheter mounting and delivery.

In accordance with an embodiment, the leaflet frame 130 comprise a shape memory material operable to flex under load and retain its original shape when the load is removed, thus allowing the leaflet frame 1 30 to self-expand from a compressed shape to a predetermined shape. In accordance with an embodiment the leaflet frame 130 is plastically deformable to be expanded by a balloon. In another embodiment the leaflet frame 130 is elastically deformable so as to be self-expanding.

Film

The film 160 is generally any sheet-like material that is biologically compatible and configured to couple to leaflets to the frame, in accordance with embodiments. It is understood that the term "film" is used generically for one or more biocompatible materials suitable for a particular purpose. The leaflets 140 are also comprised of the film 160.

In accordance with an embodiment, the biocompatible material is a film 160 that is not of a biological source and that is sufficiently flexible and strong for the particular purpose, such as a biocompatible polymer. In an embodiment, the film 160 comprises a biocompatible polymer that is combined with an elastomer, referred to as a composite.

Details of various types of film 160 are discussed below. In an embodiment, the film 160 may be formed from a generally tubular material to at least partially cover the leaflet frame 130. The film 160 can comprise one or more of a membrane, composite material, or laminate. Details of various types of film 160 are discussed below.

Leaflet

Each leaflet window 137 is provided with a biocompatible material, such as a film 160, which is coupled to a portion of the leaflet window sides 133 with the film 160 defining a leaflet 140, as shown in FIGS. 2A and 3. Each leaflet 140 defines a leaflet free edge 142 and a leaflet base 143, in accordance with an embodiment. As will be described below, it is anticipated that a plurality of embodiments of leaflet base 143 configurations may be provided. In accordance with an embodiment, the film 160 is coupled to a portion of the leaflet window sides 133 and to the leaflet window base 134 where the leaflet 140 is defined by the portion of the leaflet window sides 133 and to the leaflet window base 134. In accordance with another embodiment, the film 160 is coupled to a portion of the leaflet window sides When the leaflets 140 are in a fully open position, the prosthetic valve 100 presents a substantially circular valve orifice 102 as shown in FIG. 2C. Fluid flow is permitted through the valve orifice 102 when the leaflets 140 are in an open position.

As the leaflets 140 cycle between the open and closed positions, the leaflets 140 generally flex about the leaflet base 143 and the portion of the leaflet window sides 133 to which the leaflet are coupled. When the prosthetic valve 100 is closed, generally about half of each leaflet free edge 142 abuts an adjacent half of a leaflet free edge 142 of an adjacent leaflet 140, as shown in FIG. 2D. The three leaflets 140 of the embodiment of FIG. 2D meet at a triple point 148. The valve orifice 102 is occluded when the leaflets 140 are in the closed position stopping fluid flow.

Referring to FIG. 2D, in accordance with an embodiment, each leaflet 140 includes a central region 182 and two side regions 184 on opposite sides of the central region 182. The central region 182 is defined by a shape substantially that of a triangle defined by two central region sides 183, the leaflet base 143 and the leaflet free edge 142. The two central region sides 183 converge from the leaflet base 143 to the leaflet free edge 142.

In accordance with an embodiment, the central region 182 is substantially planar when the prosthetic valve 100 is in the closed position.

The leaflet 140 can be configured to actuate at a pressure differential in the blood caused, for example, by the contraction of a ventricle or atrium of the heart, such pressure differential typically resulting from a fluid pressure building up on one side of the prosthetic valve 100 when closed. As the pressure on an inflow side of the prosthetic valve 100 rises above the pressure on the outflow side of the prosthetic valve 100, the leaflet 140 opens and blood flows therethrough. As blood flows through the prosthetic valve 100 into a neighboring chamber or blood vessel, the pressure equalizes. As the pressure on the outflow side of the prosthetic valve 100 rises above the blood pressure on the inflow side of the prosthetic valve 100, the leaflet 140 returns to the closed position generally preventing the retrograde flow of blood through the inflow side of the prosthetic valve 100.

It is understood that the leaflet frame 130 may comprise any number of leaflet windows 137, and thus leaflets 140, suitable for a particular purpose, in accordance with embodiments. Leaflet frames 130 comprising one, two, three or more leaflet windows 137 and corresponding leaflets 140 are anticipated.

In accordance with an embodiment of a prosthetic valve 100 suitable for transcatheter placement, the prosthetic 100 may be compressed into a collapsed configuration having a smaller diameter and expanded into an expanded configuration so that the prosthetic valve 100 can be delivered via catheter in the collapsed configuration and expanded upon deployment within the tissue orifice 150 as shown in FIG. 4A. The leaflet frame 130 can be operable to recover circumferential uniformity when transitioning from the collapsed configuration to the expanded configuration.

The prosthetic valve 100 may be mounted onto a delivery catheter, suitable for a particular purpose. The diameter of the prosthetic valve 100 in the collapsed configuration is determined in part by the thickness of the frame and the leaflet thickness.

Leaflet Film

The biocompatible material that makes up the leaflet 140 can comprise any biological tissue or synthetic, biocompatible materials sufficiently compliant and flexible, such as a biocompatible polymer. In an embodiment, the leaflet 140 comprises a biocompatible polymer that is combined with an elastomer, referred to as a composite. A material according to one embodiment includes a composite material comprising an expanded fluoropolymer membrane, which comprises a plurality of spaces within a matrix of fibrils, and an elastomeric material. It should be appreciated that multiple types of fluoropolymer membranes and multiple types of elastomeric materials can be combined to form a laminate while remaining within the scope of the present disclosure. It should also be appreciated that the elastomeric material can include multiple elastomers, multiple types of non-elastomeric components, such as inorganic fillers, therapeutic agents, radiopaque markers, and the like while remaining within the scope of the present disclosure.

In accordance with an embodiment, the composite material includes an expanded fluoropolymer material made from porous ePTFE membrane, for instance as generally described in U.S. Pat. No. 7,306,729 to Bacino.

The expandable fluoropolymer, used to form the expanded fluoropolymer material described, may comprise PTFE homopolymer. In alternative embodiments, blends of PTFE, expandable modified PTFE and/or expanded copolymers of PTFE may be used. Non-limiting examples of suitable fluoropolymer materials are described in, for example, U.S. Pat. No. 5,708,044, to Branca, U.S. Pat. No. 6,541,589, to Baillie, U.S. Pat. No. 7,531,611, to Sabol et al., U.S. patent application Ser. No. 11/906,877, to Ford, and U.S. patent application Ser. No. 12/410,050, to Xu et al.

The expanded fluoropolymer membrane can comprise any suitable microstructure for achieving the desired leaflet performance. In accordance with an embodiment, the expanded fluoropolymer comprises a microstructure of nodes interconnected by fibrils, such as described in U.S. Pat. No. 3,953,566 to Gore. The fibrils radially extend from the nodes in a plurality of directions, and the membrane has a generally homogeneous structure. Membranes having this microstructure may typically exhibit a ratio of matrix tensile strength in two orthogonal directions of less than 2, and possibly less than 1.5.

In another embodiment, the expanded fluoropolymer membrane has a microstructure of substantially only fibrils, as is generally taught by U.S. Pat. No. 7,306,729, to Bacino. The expanded fluoropolymer membrane having substantially only fibrils, can possess a high surface area, such as greater than 20 $m^2/g$, or greater than 25 $m^2/g$, and in some embodiments can provide a highly balanced strength material having a product of matrix tensile strengths in two orthogonal directions of at least $1.5 \times 10^5$ $MPa^2$, and/or a ratio of matrix tensile strengths in two orthogonal directions of less than 4, and possibly less than 1.5.

The expanded fluoropolymer membrane can be tailored to have any suitable thickness and mass to achieve the desired leaflet performance. By way of example, but not limited thereto, the leaflet 140 comprises an expanded fluoropolymer membrane having a thickness of about 0.1 µm. The expanded fluoropolymer membrane can possess a mass per area of about 1.15 $g/m^2$. Membranes according to an embodiment of the invention can have matrix tensile strengths of about 411 MPa in the longitudinal direction and 315 MPa in the transverse direction.

Additional materials may be incorporated into the pores or within the material of the membranes or in between layers of membranes to enhance desired properties of the leaflet. Composite materials described herein can be tailored to have any suitable thickness and mass to achieve the desired leaflet performance. Composite materials according to embodiments can include fluoropolymer membranes and have a thickness of about 1.9 µm and a mass per area of about 4.1 $g/m^2$.

The expanded fluoropolymer membrane combined with elastomer to form a composite material provides the elements of the present disclosure with the performance attributes required for use in high-cycle flexural implant applications, such as heart valve leaflets, in various ways. For example, the addition of the elastomer can improve the fatigue performance of the leaflet by eliminating or reducing the stiffening observed with ePTFE-only materials. In addition, it may reduce the likelihood that the material will undergo permanent set deformation, such as wrinkling or creasing, that could result in compromised performance. In one embodiment, the elastomer occupies substantially all of the pore volume or space within the porous structure of the expanded fluoropolymer membrane. In another embodiment the elastomer is present in substantially all of the pores of the at least one fluoropolymer layer. Having elastomer filling the pore volume or present in substantially all of the pores reduces the space in which foreign materials can be undesirably incorporated into the composite. An example of such foreign material is calcium that may be drawn into the membrane from contact with the blood. If calcium becomes incorporated into the composite material, as used in a heart valve leaflet, for example, mechanical damage can occur during cycling open and closed, thus leading to the formation of holes in the leaflet and degradation in hemodynamics.

In an embodiment, the elastomer that is combined with the ePTFE is a thermoplastic copolymer of tetrafluoroethylene (TFE) and perfluoromethyl vinyl ether (PMVE), such as described in U.S. Pat. No. 7,462,675 to Chang et al. As discussed above, the elastomer is combined with the expanded fluoropolymer membrane such that the elastomer occupies substantially all of the void space or pores within the expanded fluoropolymer membrane to form a composite material. This filling of the pores of the expanded fluoropolymer membrane with elastomer can be performed by a variety of methods. In one embodiment, a method of filling the pores of the expanded fluoropolymer membrane includes the steps of dissolving the elastomer in a solvent suitable to create a solution with a viscosity and surface tension that is appropriate to partially or fully flow into the pores of the expanded fluoropolymer membrane and allow the solvent to evaporate, leaving the filler behind.

In one embodiment, the composite material comprises three layers: two outer layers of ePTFE and an inner layer of a fluoroelastomer disposed therebetween. Additional fluoroelastomers can be suitable and are described in U.S. Publication No. 2004/0024448 to Chang et al.

In another embodiment, a method of filling the pores of the expanded fluoropolymer membrane includes the steps of delivering the filler via a dispersion to partially or fully fill the pores of the expanded fluoropolymer membrane.

In another embodiment, a method of filling the pores of the expanded fluoropolymer membrane includes the steps of bringing the porous expanded fluoropolymer membrane into contact with a sheet of the elastomer under conditions of heat and/or pressure that allow elastomer to flow into the pores of the expanded fluoropolymer membrane.

In another embodiment, a method of filling the pores of the expanded fluoropolymer membrane includes the steps of polymerizing the elastomer within the pores of the expanded fluoropolymer membrane by first filling the pores with a prepolymer of the elastomer and then at least partially curing the elastomer.

After reaching a minimum percent by weight of elastomer, the leaflets constructed from fluoropolymer materials or ePTFE generally performed better with increasing percentages of elastomer resulting in significantly increased cycle lives. In one embodiment, the elastomer combined with the ePTFE is a thermoplastic copolymer of tetrafluoroethylene and perfluoromethyl vinyl ether, such as described in U.S. Pat. No. 7,462,675 to Chang et al., and other references that would be known to those of skill in the art. Other biocompatible polymers which can be suitable for use in leaflet 140 include but are not limited to the groups of urethanes, silicones (organopolysiloxanes), copolymers of silicon-urethane, styrene/isobutylene copolymers, polyisobutylene, polyethylene-co-poly(vinyl acetate), polyester copolymers, nylon copolymers, fluorinated hydrocarbon polymers and copolymers or mixtures of each of the foregoing.

Other Considerations

In accordance with an embodiment, the prosthetic valve 100 can be configured to prevent interference with a heart conduction system by not covering a bundle branch in the left ventricle when implanted, such as might be encountered with an aortic valve replacement procedure. For example, the prosthetic valve 100 can comprise a length of less than about 25 mm or less than about 18 mm. The prosthetic valve 100 can also comprise an aspect ratio of less than one, wherein the ratio describes the relationship between the length of the prosthetic valve 100 to the expanded, functional diameter. However, the prosthetic valve 100 can be constructed at any length and, more generally, any desirable dimension.

In a transcatheter embodiment, in a collapsed state, the prosthetic valve 100 can have a collapsed profile that is less than about 35% of the expanded profile. For example, the prosthetic valve 100 comprising a 26 mm expanded diameter can have a collapsed diameter of less than about 8 mm, or less than about 6 mm. The percent difference in diameter is dependent on dimensions and materials of the prosthetic valve 100 and its various applications, and therefore, the actual percent difference is not limited by this disclosure.

The prosthetic valve 100 can further comprise a bio-active agent. Bio-active agents can be coated onto a portion or the entirety of the film 160 for controlled release of the agents once the prosthetic valve 100 is implanted. The bio-active agents can include, but are not limited to, vasodilator, anti-coagulants, anti-platelet, anti-thrombogenic agents such as, but not limited to, heparin. Other bio-active agents can also include, but are not limited to agents such as, for example, anti-proliferative/antimitotic agents including natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); anti-platelet agents such as G(GP) IIb/IIIa inhibitors and vitronectin receptor antagonists; anti-proliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); anti-proliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anti-coagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); anti-inflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives: (cyclosporine, tacrolimus (FK-506), sirolimus (rapamycin), azathioprine, mycophenolate mofetil); angiogenic agents: vascular endothelial growth factor (VEGF), fibroblast growth factor (FGF); angiotensin receptor blockers; nitric oxide donors; anti-sense oligionucleotides and combinations thereof; cell cycle inhibitors, mTOR inhibitors, and growth factor receptor signal transduction kinase inhibitors; retenoids; cyclin/CDK inhibitors; HMG co-enzyme reductase inhibitors (statins); and protease inhibitors.

Transcatheter Delivery System

In an embodiment, with reference to FIG. 4A, a valve delivery system 500 comprises a prosthetic valve 100 having a collapsed configuration and an expanded configuration as previously described and an elongated flexible catheter 480, such as a balloon catheter, configured to deploy the prosthetic valve 100 via catheter. The catheter 480 can comprise a balloon to expand the prosthetic valve 100 and/or if required, to touch up the prosthetic valve 100 to ensure proper seating. The prosthetic valve 100 can be mounted to the distal section of the catheter 480 for delivery through the vasculature. In order to hold the valve in a collapsed configuration on the catheter 480, the valve delivery system may further comprise a removable sheath (not shown) to closely fit over the transcatheter prosthetic valve 100.

A method of delivery can comprise the steps of radially compressing a valve into its collapsed configuration onto the distal end of an elongate flexible catheter having proximal and distal ends; delivering the valve to a tissue orifice, such as a native aortic valve orifice, via a transfemoral or transapical route, and expanding the valve into the tissue orifice. The valve can be expanded by inflating a balloon.

A method of delivery can comprise the steps of radially compressing a valve into its collapsed configuration, onto the distal section of an elongated flexible catheter having proximal and distal ends. A restraint, which can be connected to a tether that passes through the orifice of valve and the lumen of the catheter, is fitted around the commissure posts 136 of the valve. The valve is then delivered to a native valve orifice, such as a native aortic valve orifice, via a route of delivery and expanded into the native orifice. The route of delivery can comprise a transfemoral or transapical route. The valve can be expanded by inflating a balloon.

Surgical Embodiments

It is appreciated that the embodiments of the prosthetic valve 100 may be surgically implanted rather than using transcatheter techniques. Embodiments of a surgically implanted prosthetic valve 100 may be substantially the same as those described above, with the addition of a sewing cuff 170 adjacent to the leaflet frame outer surface 126a, shown in FIG. 4A, in accordance with an embodiment. The sewing cuff 170, which is well known in the art, is operable to provide structure that receives suture for coupling the prosthetic valve 100 to an implant site, such as the tissue orifice 150. The sewing cuff 170 may comprise any suitable material, such as, but not limited to, double velour polyester. The sewing cuff 170 may be located circumferentially around the leaflet frame 130 or peravalvular depending from the leaflet frame 130.

Method of Making

Figure 5:
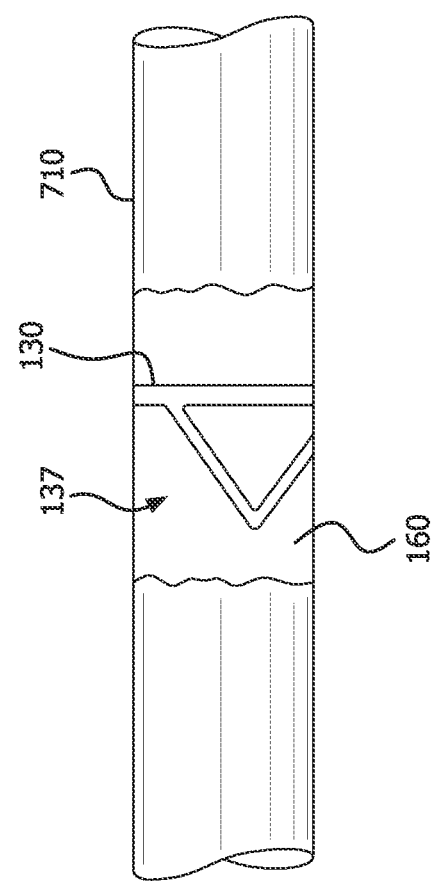
FIG. 5 is a side view of the leaflet frame on an assembly mandrel, in accordance with an embodiment.

Embodiments described herein also pertain to a method of making the prosthetic valve 100 embodiments as described herein. In order to make the various embodiments, a cylindrical mandrel 710 can be used. With reference to FIG. 5, the mandrel 710 comprises a structural form operable to receive the leaflet frame 130 thereon.

Embodiments described herein also pertain to a method of making the prosthetic valve 100 embodiments as described herein. In order to make the various embodiments, a cylindrical mandrel 710 can be used. With reference to FIG. 5, the mandrel 710 comprises a structural form operable to receive the leaflet frame 130 thereon. An embodiment of a method of making a prosthetic valve 100 comprises the steps of wrapping a first layer of film 160, e.g., a composite as described herein, into a tubular form about the mandrel 710; placing the leaflet frame 130 over the first layer of film 160, as shown in FIG. 5; forming a second layer of film 160 over the leaflet frame 130; thermally setting the assembly; receiving the assembly over a cutting mandrel 712 as shown in FIGS. 6A and 6B; cutting the film 160 across the leaflet window top within the leaflet window 137 resulting in the prosthetic valve 100 of FIGS. 2A and 2B. In FIGS. 2A and 2B, the leaflets 140 are shown slightly open as they are when held by the cutting mandrel 712. It is understood that a fully closed prosthetic valve 100 will have the leaflet free edges 142 of the leaflets 140, including the triple point 148, coming together to coapt under the influence of downstream fluid pressure which results in closing the valve to prevent downstream blood from flowing retrograde through the valve.

Example

In exemplary embodiments, a heart valve having polymeric leaflets formed from a composite material having an expanded fluoropolymer membrane and an elastomeric material and joined to a semi-rigid, non-collapsible metallic frame, and further a having strain relief was constructed according to the following process:

A valve frame was laser machined from a length of MP35N cobalt chromium tube hard tempered with an outside diameter of 26.0 mm and a wall thickness of 0.6 mm in the shape. The frame was electro-polished resulting in 0.0126a mm material removal from each surface and leaving the edges rounded. The frame was exposed to a surface roughening step to improve adherence of leaflets to the frame. The frame was cleaned by submersion in an ultrasonic bath of acetone for approximately five minutes. The entire metal frame surface was then subjected to a plasma treatment using equipment (e.g. PVA TePLa America, Inc Plasma Pen, Corona, Calif.) and methods commonly known to those having ordinary skill in the art. This treatment also served to improve the wetting of the fluorinated ethylene propylene (FEP) adhesive.

FEP powder (Daikin America, Orangeburg N.Y.) was then applied to the frame. More specifically, the FEP powder was stirred to form an airborne "cloud" in an enclosed blending apparatus, such as a standard kitchen type blender, while the frame is suspended in the cloud. The frame was exposed to the FEP powder cloud until a layer of powder was adhered to the entire surface of the frame. The frame was then subjected to a thermal treatment by placing it in a forced air oven set to 320° C. for approximately three minutes. This caused the powder to melt and adhere as a thin coating over the entire frame. The frame was removed from the oven and left to cool to approximately room temperature.

A polymeric strain relief was attached to the frame in the following manner. A thin (122 µm) walled sintered 15 mm diameter ePTFE tube was disposed on a 24.5 mm vented metal mandrel by stretching radially over a tapered mandrel. Two layers of a substantially nonporous ePTFE membrane with a continuous FEP coating was circumferentially wrapped on the mandrel with the FEP side towards the mandrel. The wrapped mandrel was placed in a convection oven set to 320° C., heated for 20 minutes, and air cooled to room temperature. The ePTFE and substantially nonporous ePTFE membrane combined to serve as an inner release liner and was perforated using a scalpel blade to communicate pressure between the vent holes in the mandrel. This entire release liner is removed in a later step.

A 5 cm length of the thick (990µ) walled partially sintered 22 mm inner diameter ePTFE tube (density=0.3 g/cm³) was disposed onto the 24.5 mm vented metal mandrel with release liner. The ePTFE tube inner diameter was enlarged by stretching it on a tapered mandrel to accommodate the larger mandrel diameter.

A thin (4 µm) film of type 1 FEP (ASTM D3368) was constructed using melt extrusion and stretching. One layer of the FEP was wrapped over the 5 cm length of the ePTFE tube.

The FEP powder coated frame was disposed onto the vented metal mandrel generally in the middle of the 5 cm span of ePTFE tube and FEP film.

One layer of the FEP was wrapped over the frame and 5 cm length of the ePTFE tube.

A second 5 cm length of the 990 µm thick/22 mm inner diameter ePTFE tube was disposed onto the assembly layered onto 24.5 mm vented metal mandrel by stretching its radius over a tapered mandrel to accommodate the larger construct diameter.

A substantially nonporous ePTFE membrane was configured into a cylinder at a diameter larger than the construct and placed over the assembly, referred to as sacrificial tube. Sintered ePTFE fiber (e.g. Gore® Rastex® Sewing Thread, Part #S024T2, Newark Del.) was used to seal both ends of the sacrificial tube against the mandrel.

The assembly, including the mandrel, was heated in a convection oven (temperature set point of 390° C.) capable of applying pneumatic pressure of 100 psi external to the sacrificial tube described above while maintaining a vacuum internal to the mandrel. The assembly was cooked for 40 minutes such that the mandrel temperature reached approximately 360° C. (as measured by a thermocouple direct contact with the inner diameter of the mandrel). The assembly was removed from the oven and allowed to cool to approximately room temperature while still under 100 psi pressure and vacuum.

The Rastex® fiber and sacrificial tube was then removed. Approximately 30 psi of pressure was applied to the internal diameter of the mandrel to assist in removal of the assembly. The inner release liner was peeled away from the internal diameter of the assembly by inverting the liner and axially pulling it apart.

Excess polymeric material was trimmed with a scalpel and removed from the leaflet windows and bottom of the frame leaving approximately 0.5 to 1.0 mm of material overhang.

A leaflet material was then prepared. A membrane of ePTFE was manufactured according to the general teachings described in U.S. Pat. No. 7,306,729. The ePTFE membrane had a mass per area of 0.452 g/m², a thickness of about 508 nm, a matrix tensile strength of 705 MPa in the longitudinal direction and 385 MPa in the transverse direction. This membrane was imbibed with a fluoroelastomer. The copolymer consists essentially of between about 65 and 70 weight percent perfluoromethyl vinyl ether and complementally about 35 and 30 weight percent tetrafluoroethylene.

The fluoroelastomer was dissolved in Novec HFE7500 (3M, St Paul, Minn.) in a 2.5% concentration. The solution was coated using a mayer bar onto the ePTFE membrane (while being supported by a polypropylene release film) and dried in a convection oven set to 145° C. for 30 seconds. After 2 coating steps, the final ePTFE/fluoroelastomer or composite had a mass per area of 1.75 g/m², 29.3% fluoropolymer by weight, a dome burst strength of about 8.6 KPa, and thickness of 0.81 µm.

The frame encapsulated with polymeric material defining a strain relief was then attached to the leaflet material in a cylindrical or tubular shape in the following manner. A release liner was disposed on a 24.5 mm vented mandrel and perforated using a scalpel blade to communicate pressure between the vent holes in the mandrel.

The frame with polymeric strain relief was disposed onto the release liner covering the vented metal mandrel generally in the middle of the 100 cm span of the mandrel.

Sixty-two layers of leaflet material were wrapped over the frame and 100 cm length of the mandrel. Excess leaflet material was trimmed away with a scalpel from the mandrel adjacent to the vent holes.

A sacrificial tube was placed over the assembly and Rastex® fiber was used to seal both ends of the sacrificial tube against the mandrel.

The assembly, including the mandrel, was heated in a convection oven (temperature set point of 390° C.) capable of applying pneumatic pressure of 100 psi external to the sacrificial tube described above while maintaining a vacuum internal to the mandrel. The assembly was cooked for 23 minutes such that the mandrel temperature reached approximately 285° C. (as measured by a thermocouple direct contact with the inner diameter of the mandrel). The assembly was removed from the oven and allowed to cool to approximately room temperature while still under 100 psi pressure and vacuum.

The Rastex® fiber and sacrificial tube were then removed. Approximately 30 psi of pressure was applied inside the mandrel to assist in removal of the assembly. The inner release liner was peeled away from the internal diameter of the assembly by inverting the liner and axially pulling it apart.

The cylindrical shape of the frame and leaflet assembly was then molded into the final closed leaflet geometry in the following manner. The assembly was placed onto a 24.5 mm vented mandrel with a cavity defining the closed geometry of the leaflets.

Rastex® fiber was used to seal both ends of the leaflet tube against the circumferential grooves in the mandrel.

The assembly, including the mandrel, was heated in a convection oven (temperature set point of 390° C.) capable of applying pneumatic pressure of 100 psi external to the sacrificial tube described above while maintaining a vacuum internal to the mandrel. The assembly was cooked for 23 minutes such that the mandrel temperature reached approximately 285° C. (as measured by a thermocouple direct contact with the inner diameter of the mandrel). The assembly was removed from the oven and allowed to cool to approximately room temperature while still under 100 psi pressure and vacuum. The Rastex® fiber was then removed and approximately 10 psi of pressure was applied to the internal diameter of the mandrel to assist in removal of the assembly.

Excess leaflet material was trimmed generally along the free edge line depicted in a cavity mold 714 of the cutting mandrel 712 shown in FIGS. 6A and 6B.

The final leaflet was comprised of 28.22% fluoropolymer by weight with a thickness of 50.3 µm. Each leaflet had 62 layers of the composite and a ratio of thickness/number of layers of 0.81 µm.

The resulting prosthetic valve 100, as shown in FIG. 2A-2D, includes leaflets 140 formed from a composite material with more than one fluoropolymer layer having a plurality of pores and an elastomer present in substantially all of the pores of the more than one fluoropolymer layer. Each leaflet 104 is movable between a closed position, shown in FIG. 2D, in which blood is substantially prevented from flowing through the valve assembly, and an open position, shown in FIG. 2C, in which blood is allowed to flow through the valve assembly. Thus, the leaflets 104 of the prosthetic valve 100 cycle between the closed and open positions generally to regulate blood flow direction in a human patient.

The hydrodynamic performance was measured prior to accelerated wear testing. The performance values were: EOA=2.4 cm$^2$ and regurgitant fraction=11.94%.

The performance of the valve leaflets was characterized on a real-time pulse duplicator that measured typical anatomical pressures and flows across the valve. The flow performance was characterized by the following process:

The valve assembly was potted into a silicone annular ring (support structure) to allow the valve assembly to be subsequently evaluated in a real-time pulse duplicator. The potting process was performed according to the recommendations of the pulse duplicator manufacturer (ViVitro Laboratories Inc., Victoria BC, Canada)

The potted valve assembly was then placed into a real-time left heart flow pulse duplicator system. The flow pulse duplicator system included the following components supplied by VSI Vivitro Systems Inc., Victoria BC, Canada: a Super Pump, Servo Power Amplifier Part Number SPA 3891; a Super Pump Head, Part Number SPH 5891B, 38.320 cm$^2$ cylinder area; a valve station/fixture; a Wave Form Generator, TriPack Part Number TP 2001; a Sensor Interface, Part Number VB 2004; a Sensor Amplifier Component, Part Number AM 9991; and a Square Wave Electro Magnetic Flow Meter, Carolina Medical Electronics Inc., East Bend, N.C., USA.

In general, the flow pulse duplicator system uses a fixed displacement, piston pump to produce a desired fluid flow through the valve under test.

The heart flow pulse duplicator system was adjusted to produce the desired flow (5 L/minutes), mean pressure (15 mmHg), and simulated pulse rate (70 bpm). The valve under test was then cycled for about 5 to 20 minutes.

Pressure and flow data were measured and collected during the test period, including right ventricular pressures, pulmonary pressures, flow rates, and pump piston position. Parameters used to characterize the valve are effective orifice area and regurgitant fraction. The effective orifice area (EOA), which can be calculated as follows: $EOA(cm^2)=Q_{rms}/(51.6*(\Delta P)^{1/2})$ where $Q_{rms}$ is the root mean square systolic/diastolic flow rate (cm$^3$/s) and $\Delta P$ is the mean systolic/diastolic pressure drop (mmHg).

Another measure of the hydrodynamic performance of a valve is the regurgitant fraction, which is the amount of fluid or blood regurgitated through the valve divided by the stroke volume.

L As used in this application, the surface area per unit mass, expressed in units of m$^2$/g, was measured using the Brunauer-Emmett-Teller (BET) method on a Coulter SA3100Gas Adsorption Analyzer, Beckman Coulter Inc. Fullerton Calif., USA. To perform the measurement, a sample was cut from the center of the expanded fluoropolymer membrane and placed into a small sample tube. The mass of the sample was approximately 0.1 to 0.2 g. The tube was placed into the Coulter SA-Prep Surface Area Outgasser (Model SA-Prep, P/n 5102014) from Beckman Coulter, Fullerton Calif., USA and purged at about 110° C. for about two hours with helium. The sample tube was then removed from the SA-Prep Outgasser and weighed. The sample tube was then placed into the SA3100 Gas adsorption Analyzer and the BET surface area analysis was run in accordance with the instrument instructions using helium to calculate the free space and nitrogen as the adsorbate gas.

Bubble point and mean flow pore size were measured according to the general teachings of ASTM F31 6-03 using a capillary flow Porometer, Model CFP 1500AEXL from Porous Materials, Inc., Ithaca N.Y., USA. The sample membrane was placed into the sample chamber and wet with SilWick Silicone Fluid (available from Porous Materials Inc.) having a surface tension of about 20.1 dynes/cm. The bottom clamp of the sample chamber had an about 2.54 cm diameter hole. Isopropyl alcohol was used as the test fluid. Using the Capwin software version 7.73.012 the following parameters were set as specified in the table below. As used herein, mean flow pore size and pore size are used interchangeably.

| Parameter | Set Point |
|---|---|
| Maxflow (cm³/m) | 200000 |
| Bublflow (cm³/m) | 100 |
| F/PT (old bubltime) | 50 |
| Minbpress (PSI) | 0 |
| Zerotime (sec) | 1 |
| V2incr (cts) | 10 |
| Preginc (cts) | 1 |
| Pulse delay (sec) | 2 |
| Maxpre (PSI) | 500 |
| Pulse width (sec) | 0.2 |
| Mineqtime (sec) | 30 |
| Presslew (cts) | 10 |
| Flowslew (cts) | 50 |
| Eqiter | 3 |
| Aveiter | 20 |
| Maxpdif (PSI) | 0.1 |
| Maxfdif (PSI) | 50 |
| Sartp (PSI) | 1 |
| Sartf (cm³/m) | 500 |

Membrane thickness was measured by placing the membrane between the two plates of a Käfer FZ1000/30 thickness snap gauge Käfer Messuhrenfabrik GmbH, Villingen-Schwenningen, Germany. The average of the three measurements was reported.

The presence of elastomer within the pores can be determined by several methods known to those having ordinary skill in the art, such as surface and/or cross section visual, or other analyses. These analyses can be performed prior to and after the removal of elastomer from the leaflet.

Membrane samples were die cut to form rectangular sections about 2.54 cm by about 15.24 cm to measure the weight (using a Mettler-Toledo analytical balance model AG204) and thickness (using a Käfer Fz1000/30 snap gauge). Using these data, density was calculated with the following formula: $\rho = m/w*l*t$, in which: $\rho$=density (g/cm³); m=mass (g), w=width (cm), l=length (cm), and t=thickness (cm). The average of three measurements was reported.

Tensile break load was measured using an INSTRON 122 tensile test machine equipped with flat-faced grips and a 0.445 kN load cell. The gauge length was about 5.08 cm and the cross-head speed was about 50.8 cm/min. The sample dimensions were about 2.54 cm by about 15.24 cm. For longitudinal measurements, the longer dimension of the sample was oriented in the highest strength direction. For the orthogonal MTS measurements, the larger dimension of the sample was oriented perpendicular to the highest strength direction. Each sample was weighed using a Mettler Toledo Scale Model AG204, then the thickness measured using the Käfer FZ1000/30 snap gauge. The samples were then tested individually on the tensile tester. Three different sections of each sample were measured. The average of the three maximum loads (i.e., peak force) measurements was reported. The longitudinal and transverse matrix tensile strengths (MTS) were calculated using the following equation: MTS=(maximum load/cross-section area)*(bulk density of PTFE)/(density of the porous membrane), wherein the bulk density of the PTFE was taken to be about 2.2 g/cm³. Flexural stiffness was measured by following the general procedures set forth in ASTM D790. Unless large test specimens are available, the test specimen must be scaled down. The test conditions were as follows. The leaflet specimens were measured on a three-point bending test apparatus employing sharp posts placed horizontally about 5.08 mm from one another. An about 1.34 mm diameter steel bar weighing about 80 mg was used to cause deflection in the y (downward) direction, and the specimens were not restrained in the x direction. The steel bar was slowly placed on the center point of the membrane specimen. After waiting about 5 minutes, the y deflection was measured. Deflection of elastic beams supported as above can be represented by: $d = F*L^3/48*EI$, where F (in Newtons) is the load applied at the center of the beam length, L (meters), so L=½ distance between suspending posts, and EI is the bending stiffness (Nm). From this relationship the value of EI can be calculated. For a rectangular cross-section: $I = t^3 * w/12$, where I=cross-sectional moment of inertia, t=specimen thickness (meters), w=specimen width (meters). With this relationship, the average modulus of elasticity over the measured range of bending deflection can be calculated.

It will be apparent to those skilled in the art that various modifications and variations can be made in the present embodiments without departing from the spirit or scope of the embodiments. Thus, it is intended that the present embodiments cover the modifications and variations of this invention provided they come within the scope of the appended claims and their equivalents.

What is claimed:

1. A prosthetic valve comprising:
a leaflet frame; and
a plurality of leaflets that are coupled to the leaflet frame, each leaflet including two leaflet sides, a leaflet free edge and a leaflet base, wherein the leaflet base of each leaflet has a truncation in which the leaflet in cross section shows a line in an alpha plane onto the leaflet frame, the leaflet frame having a tubular shape, the leaflet frame defining a plurality of leaflet windows wherein each of the leaflet windows includes two leaflet window sides, a leaflet window base, and a leaflet window top; and
a film that is coupled to the leaflet frame and defining at least one leaflet extending from each of the leaflet windows, wherein each leaflet has a shape of an isosceles trapezoid having two leaflet window sides, a leaflet base and a leaflet free edge opposite the leaflet base, wherein the two leaflet sides diverge from the leaflet base, wherein the leaflet base is flat, wherein the leaflet base is coupled to the window base and wherein each of the two leaflet sides are coupled to one of the two leaflet window sides, wherein each leaflet includes a central region and two side regions on opposite sides of the central region, wherein the central region is defined by a shape of an isosceles triangle defined by two central region sides, the leaflet base and the leaflet free edge, wherein the two central region sides converge from the leaflet base, and wherein each of the side regions have a shape of a triangle and each are defined by one of the central region sides, one of the leaflet sides, and the leaflet free edge, wherein each of the two side regions and the central region are planar when the prosthetic valve is in a closed position under unpressurized conditions.

2. The prosthetic valve of claim 1, in which the truncation of each leaflet is located inferior and exterior to a line joining apices of two adjacent commissural posts.

3. The prosthetic valve of claim 1, in which the truncation is a straight line across the leaflet base of the leaflet and perpendicular to a valve axis.

4. The prosthetic valve of claim 1, wherein the leaflet frame comprises a leaflet frame first end and a leaflet frame second end opposite the leaflet frame first end, the leaflet window having a shape determined, at least in part, by wrapping a two dimensional isosceles trapezoid onto the tubular shape of the leaflet frame, the isosceles trapezoid having a base and two sides that diverge from the base, and wherein a side from adjacent isosceles trapezoids meet at the leaflet frame second end.

5. The prosthetic valve of claim 4, further comprising a commissure post extending axially from where the adjacent isosceles trapezoids meet, the commissure post having a length extending to the leaflet frame second end.

6. The prosthetic valve of claim 1, wherein the film is coupled to an outer surface of the leaflet frame, wherein the film defines the leaflet extending from each of the leaflet windows.

7. The prosthetic valve of claim 1, wherein the film is coupled to an inner surface of the leaflet frame, wherein the film defines the leaflet extending from each of the leaflet windows.

8. The prosthetic valve of claim 1, wherein the film is coupled to an inner surface and an outer surface of the leaflet frame, wherein the film defines the leaflet extending from each of the leaflet windows.

9. The prosthetic valve of claim 1, wherein the leaflet frame defines three interconnected leaflet windows having a triangular shape.

10. The prosthetic valve of claim 1, wherein a leaflet window side of one leaflet window is interconnected with a leaflet window side of an adjacent leaflet window.

11. The prosthetic valve of claim 1, wherein the leaflet frame comprises a plurality of spaced apart leaflet windows each defining an isosceles triangle interconnected by a base element therebetween, wherein each leaflet window side is defined by a side of one triangle and a side of an adjacent triangle, and wherein each leaflet window base is defined by the base element.

12. The prosthetic valve of claim 1, wherein the leaflet frame comprises a plurality of spaced apart interconnected leaflet windows, each leaflet window defining isosceles trapezoids, wherein each leaflet window side is defined by sides of the isosceles trapezoid, and wherein each leaflet window base is defined by a base element.

13. The prosthetic valve of claim 1, wherein the prosthetic valve comprises a collapsed configuration and an expanded configuration for transcatheter delivery.

14. The prosthetic valve of claim 1, wherein the leaflet comprises a polymeric material.

15. The prosthetic valve of claim 14, wherein the leaflet comprises a laminate.

16. The prosthetic valve of claim 15, wherein the laminate has more than one layer of a fluoropolymer membrane.

17. The prosthetic valve of claim 1, wherein the leaflet comprises a film having at least one layer of a fluoropolymer membrane having a plurality of pores and an elastomer present in the pores of the at least one layer of the fluoropolymer membrane.

18. The prosthetic valve of claim 17, wherein the film comprises less than about 80% fluoropolymer membrane by weight.

19. The prosthetic valve of claim 17, wherein the elastomer comprises (per)fluoroalkylvinylethers (PAVE).

20. The prosthetic valve of claim 17, wherein the elastomer comprises a copolymer of tetrafluoroethylene and perfluoromethyl vinyl ether.

21. The prosthetic valve of claim 17, wherein the fluoropolymer membrane comprises ePTFE.

* * * * *